United States Patent [19]

Lee et al.

[11] Patent Number: 4,720,553
[45] Date of Patent: Jan. 19, 1988

[54] METHOD FOR SYNTHESIZING N-AMINOPHTHALIMIDE

[75] Inventors: George E. Lee, Somerville; Robert J. Heffner, Manville, both of N.J.

[73] Assignee: Hoechst-Roussel Pharmaceuticals Inc., Somerville, N.J.

[21] Appl. No.: 851,844

[22] Filed: Apr. 14, 1986

[51] Int. Cl.$^4$ .......................... C07D 209/48
[52] U.S. Cl. .................................. 548/475
[58] Field of Search ........................ 548/475

[56] References Cited

U.S. PATENT DOCUMENTS 2,657,169 10/1953 Ligett et al. ........................ 548/475

OTHER PUBLICATIONS

H. Drew et al, J. Chem. Soc., 1937, pp. 16–33.
J. Krause et al, J. Org. Chem., 37, 2040–2042 (1972).
W. Flitsch et al, Chem. Ber. 102, 3268–3276 (1969).

Primary Examiner—Mary E. Ceperley
Attorney, Agent, or Firm—Tatsuya Ikeda

[57] ABSTRACT

There is described an improved method for synthesizing N-aminophthalimide from phthalimide and hydrazine wherein the reaction is conducted in a medium consisting essentially of water and alcohol at a volume ratio within the range of from 80:20 to 20:80 at a temperature within the range of from −5° C. to 35° C., said alcohol being methanol, ethanol, n-propanol, isopropanol or a mixture thereof.

4 Claims, No Drawings

METHOD FOR SYNTHESIZING N-AMINOPHTHALIMIDE

This invention relates to an improved method for synthesizing N-aminophthalimide from phthalimide and hydrazine.

Reaction of phthalimide with hydrazine usually gives a mixture of N-aminophthalimide (2-amino-1H-isoindole,1,3(2H)dione), II, and 2,3dihydro-1,4-phthalazine dione, III, and the relative amounts of the two compounds vary over a wide range depending upon the reaction conditions including the reaction medium used, reaction temperature and time.

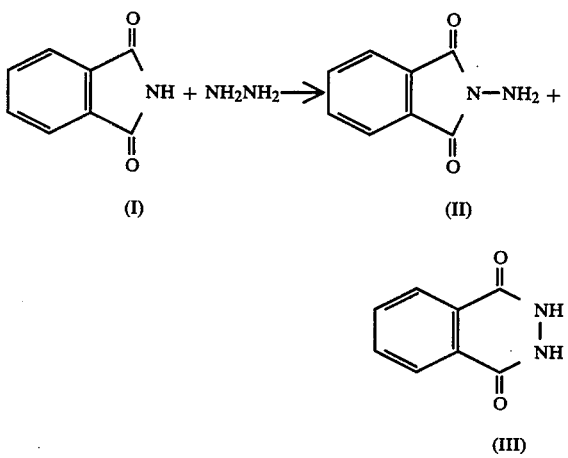

N-aminophthalimide is a useful compound for various applications, for instance, as an intermediate for synthesizing other organic compounds which have pharmaceutical activities. Commercial preparation of pharmacuetical intermediates is generally conducted in batch processes due to the limited nature of the quantities of intermediate needed. It is the primary object of this invention to provide a commercially advantageous method for synthesizing N-aminophthalimide from phthalimide and hydrazine.

The aforementioned reaction itself has been known for a long time, but the reported reaction conditions and/or procedures are not necessarily satisfactory, especially for large scale commercial work. Thus, for instance, Drew and Hatt (J. Chem. Soc. 1937, pp 16–26) disclose an experiment in which a mixture prepared from compound I, hydrazine hydrate and ethanol is shaken for 2 minutes at room temperature and thereafter quickly heated and refluxed for 3 minutes and then quenched with water to obtain about 40% yield of compound II. Such a procedure is clearly not suitable for use on an industrial scale where reactors with slow heat-up and cool-down times are used.

Krause et al., J. Org. Chem. Volume 37, pp. 2040–2042 (1972) disclose a reaction sequence wherein N-tert-butyloxycarbonylaminophthalimide is prepared from phthalic anhydride and t-butyl carbazate and thereafter hydrolyzed under an acidic condition and the hydrolysis product is neutralized to give compound II in about 81% yield.

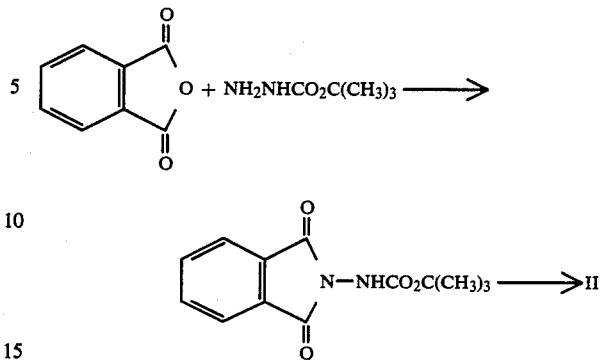

This reaction sequence, however, requires a multistep synthesis of t-butyl carbazate, which is not economically advantageous.

We have found that a satisfactory yield of the target compound II is obtained within a practically reasonable reaction period by use of a reaction medium consisting essentially of water and alcohol at a volume ratio within the range of from 80:20 to 20:80, and by conducting the reaction at a temperature within the range of from $-5°$ C. to 35° C. The term alcohol as used in the specification and the appended claims shall mean methanol, ethanol, n-propanol, iso-propanol or a mixture thereof. A more preferred volume ratio between water and alcohol is between 60:40 and 40:60, and the most preferred ratio is around 50:50. The term volume ratio is based on the volumes of water and alcohol at 25° C. prior to the preparation of the mixture. A more preferred reaction temperature is between $-5°$ C. and 5° C., and the most preferred temperature is around 0° C.

The method of this invention, which is characterized by the reaction medium and the reaction temperature specified above, provides a commercially advantageous method of synthesizing compound II from phthalimide, I, and hydrazine, inasmuch as the yield of compound II is higher than the yield obtained when ethanol is used as a medium and a reflux condition is used, and yet the reaction period is still practically reasonable.

With regard to alcohol used for the reaction medium, methanol and ethanol are preferred.

The selectivity of the reaction to compound II generally increases with decrease in the reaction temperature, but the reaction rate decreases with decrease in the temperature. Nonetheless, it has been found that the reaction proceeds at a reasonable rate even near the lower end of the temperature range specified above. Thus, for instance, under a typical condition of 0° C. and water:methanol=50:50, a suitable reaction time is about 3 to 5 hours, at the end of which compound II is obtained at about 62% yield based on compound I. Generally speaking, the reaction rate increases with increase in the proportion of water in the reaction medium. The reaction period should be chosen judiciously by taking into consideration the fact that in order to obtain an economically advantageous result, the conversion of the starting compound I has to reach a reasonable level and at the same time the selectivity to compound II has to be reasonably high. The selectivity does not stay constant with time, but instead it generally varies with time and usually too long a reaction time results in sacrifice of selectivity. Usually, suitable reaction period is between 1 and 10 hours, and the optimal reaction period can be determined without difficulty by monitoring the product composition of the reaction as a function of time by use of known analytical techniques, for instance, high performance liquid chromatography (HPLC).

For conducting the reaction according to the method of this invention, usually a solution of hydrazine in a water/alcohol mixture is prepared first and then phthalimide is added to the solution, but the sequence of addition is not critical. After the reaction has been carried out for a suitable predetermined period of time, compound II is separated from other compounds of the reaction mixture by a routine procedure. Thus, typically, excess water is added to the reaction mixture in order to precipitate compound II which is collected by filtration. Quite often, it is not necessary to obtain compound II in a highly purified form for the purpose of using it for the synthesis of useful derivatives. Although it depends upon the reaction condition, the primary impurity in the product collected in the manner described immediately above is usually unreacted compound I. Attempts to remove compound I from the product usually results in the formation of more byproduct, namely, compound III.

The reaction is usually conducted as a batch process, but it may be conducted as a continuous process. In the latter case, particularly when there is back mixing in the reaction system, the term reaction period should be interpreted as the average residence time of the reactant molecules involved in the reaction.

There are no particular limitations as to the starting concentrations of compound I and hydrazine in the reaction medium. Typically, they are 0.5–5 moles/liter, hydrazine being usually in molar excess over compound I. When a hydrated form of hydrazine such as hydrazine monohydrate is used as a starting material, the volume ratio between water and alcohol defined above takes into account the hydration water.

The following example is presented for the purpose of illustrating this invention.

EXAMPLE

The aforementioned reaction between phthalimide and hydrazine was conducted under various conditions shown in Table 1. In each run, the reaction mixture was quenched with excess water and the resultant precipitate was collected by filtration. The product mixture was analyzed by HPLC. The yield of compound II in Table 1 is based on the starting molar amount of compound I. In conducting the runs, it was observed that generally the yield of compound II did not remain constant with time. The values of reaction time listed in Table 1 represent the time we decided to quench the reaction and isolate the product, and they are not necessarily the optimal reaction time for obtaining the best yield of compound II.

TABLE 1

| Run | Amount of (I) (mole) | Molar ratio, hydrazine/ (I) | Solvent (ml) | Temp. (C.) | Time (hrs) | Yield of (II) |
|---|---|---|---|---|---|---|
| 1 | 0.5 | 1.1 | MeOH/$H_2O$ (50:50) 370 | 0° | 9.0 | 62% |
| 2 | 0.5 | 1.1 | EtOH/$H_2O$ (50:50) 370 | 0° | 9.0 | 63% |
| 3 | 0.5 | 1.25 | MeOH/$H_2O$ (50:50) 370 | 0° | 5.0 | 63% |
| 4 | 0.5 | 1.25 | MeOH/$H_2O$ (25:75) 370 | 0° | 5.0 | 45% |

We claim:

1. A method of synthesizing N-aminophthalimide wherein phthalimide and hydrazine are reacted in a reaction medium consisting essentially of water and alcohol at a volume ratio within the range of from 80:20 to 20:80 at a temperature within the range of from −5° C. to 35° C., said alcohol being methanol, ethanol, n-propanol, iso-propanol or a mixture thereof.

2. The method as defined in claim 1, wherein the reaction is conducted at a temperature within the range of from −5° C. to 5° C.

3. The method as defined in claim 1, wherein the volume ratio between water and alcohol is within the range of from 60:40 to 40:60.

4. The method as defined in claim 2, wherein the volume ratio between water and alcohol is within the range of from 60:40 to 40:60.

* * * * *